United States Patent [19]

Kurtz et al.

[11] 4,296,748
[45] Oct. 27, 1981

[54] UNDERWATER DRAINAGE APPARATUS WITH SEPARABLE SUCTION CONTROL CHAMBER

[75] Inventors: Leonard D. Kurtz, Woodmere; Robert E. Bidwell, Melville, both of N.Y.

[73] Assignee: BioResearch Inc., Farmingdale, N.Y.

[21] Appl. No.: 52,825

[22] Filed: Jun. 27, 1979

[51] Int. Cl.³ .............................................. A61M 1/00
[52] U.S. Cl. .................................... 128/276; 128/762
[58] Field of Search ................ 181/233, 235; 137/205; 15/353; 206/363; 128/276, 277, 278, 762, 767

[56] References Cited

U.S. PATENT DOCUMENTS

| | | | |
|---|---|---|---|
| 3,782,497 | 1/1974 | Bidwell et al. | 181/233 |
| 3,847,152 | 11/1974 | Schachet | 128/276 |
| 4,015,603 | 4/1977 | Kurtz et al. | 128/276 |
| 4,105,031 | 8/1978 | Kurtz et al. | 128/276 |
| 4,112,948 | 9/1978 | Kurtz et al. | 128/276 |

*Primary Examiner*—Stephen C. Pellegrino
*Assistant Examiner*—J. L. Kruter
*Attorney, Agent, or Firm*—Larson and Taylor

[57] ABSTRACT

An underwater drainage apparatus is provided which is convertible from a two bottle system including a collection chamber and underwater seal chamber to a three bottle system including a suction control chamber. A rubber diaphragm is provided in the container for the collection chamber and underwater seal and a needle having a large bore is provided in the suction control chamber. Trackways on the suction control chamber and collection chamber interfit so that the suction control chamber can be slid into position wherein the needle penetrates the diaphragm to place the suction control chamber in fluid communication with the underwater seal chamber and collection chamber.

5 Claims, 4 Drawing Figures

U.S. Patent     Oct. 27, 1981     4,296,748
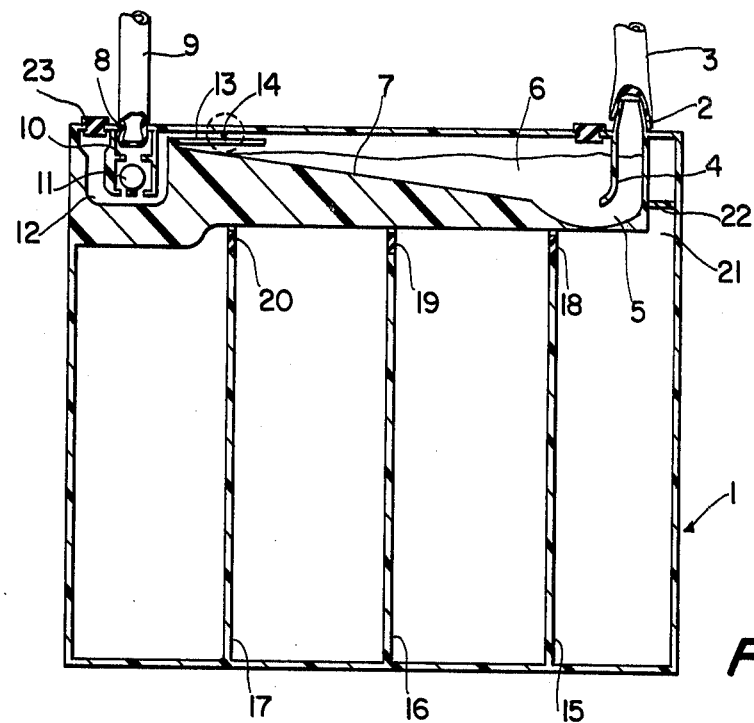
FIG. 1
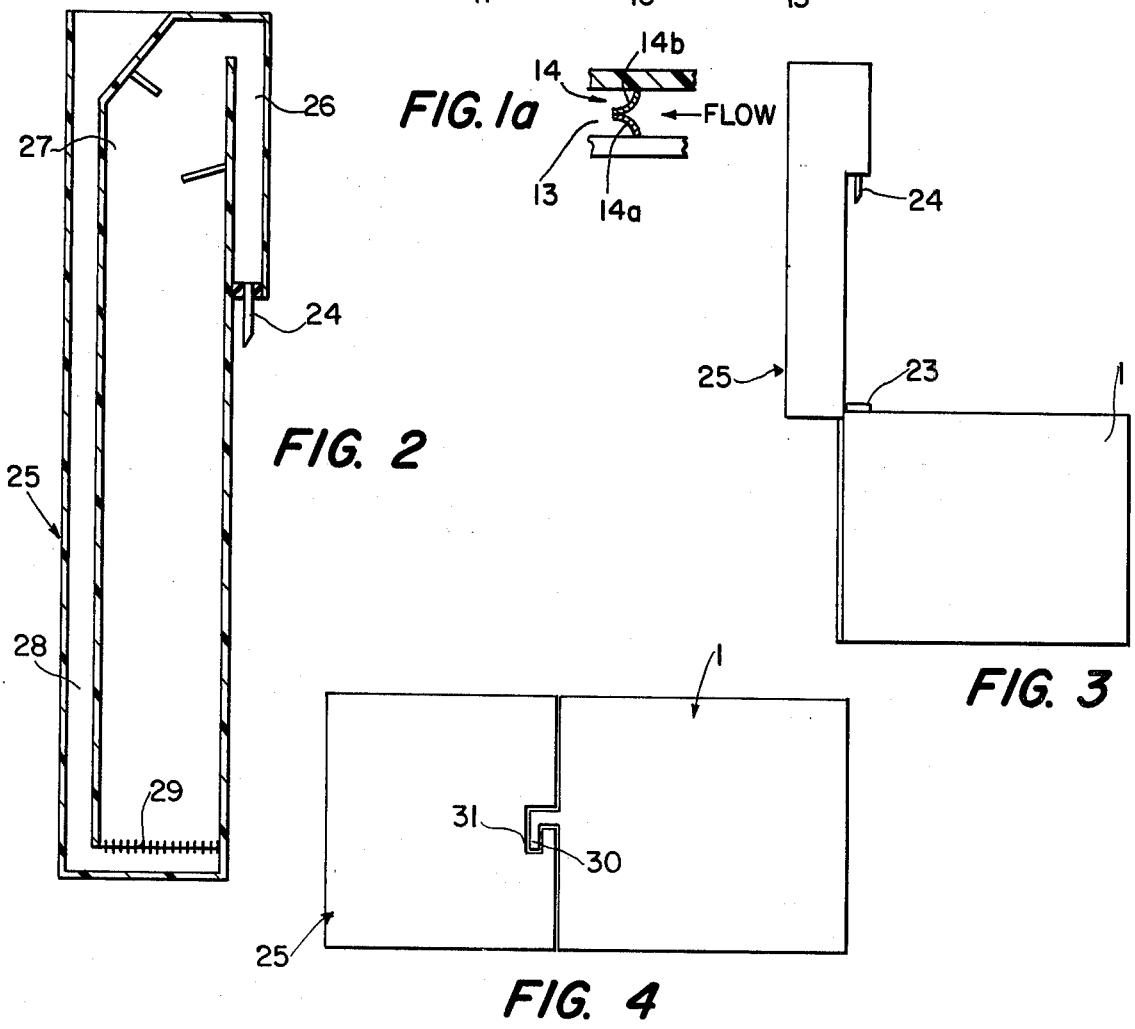
FIG. 1a
FIG. 2
FIG. 3
FIG. 4

UNDERWATER DRAINAGE APPARATUS WITH SEPARABLE SUCTION CONTROL CHAMBER

FIELD OF THE INVENTION

The present invention relates to an underwater drainage apparatus and more particularly to a drainage apparatus which may be used as a two chambered system having a collection chamber and underwater seal chamber and as a three chambered system including a collection chamber, underwater seal chamber and a suction control chamber.

Description of the Prior Art

It is necessary to provide means for removing fluids from the pleural cavity of a patient following an operation on the lungs or heart, or in the case of a foreign object which penetrates the pleural cavity such as a stab wound, or the like. Usually such drainage devices are also provided with means for maintaining a predetermined amount of suction on the pleural cavity so that the lungs can expand and contract for normal breathing. The degree of suction may be regulated by the suction pump itself, by having an adjustable suction regulator or alternatively, the drainage apparatus may be provided with a suction control chamber which may maintain the degree of suction within the pleural cavity at any desired level. Frequently, in the treatment of a certain class of problem in the pleural cavity, it is unnecessary to provide any suction and the only need is for a collection chamber to collect fluids passing out of the pleural cavity through the thoracotomy tube.

There have been no prior art underwater drainage devices which can readily be modified to accomodate the above stated operational requirements. U.S. Pat. Nos. 3,363,626 and 3,363,627 disclose one piece underwater drainage devices which include a collection chamber, underwater seal chamber and suction control chamber. These devices are ideal for use where suction control is required but, are not readily adapted to use as a two chambered device where no suction control is required.

U.S. Pat. No. 4,015,603 discloses essentially a two chambered device utilizing a collection chamber and underwater seal chamber and which is well suited for use with a vacuum system having a regulated suction control or for use as a two chambered device where no suction is necessary and the outlet may be left open to atmosphere. However, there is no means for modifying the apparatus shown in this patent to provide for use with conventional wall suction as used in a hospital where no suction control is provided.

U.S. Pat. No. 3,847,152 discloses a modular thoracic drainage device comprising a plurality of separable bottles which may be interconnected to make up specific combinations as required. However, this device lacks simplicity and ease of assembly which are required for emergency use.

U.S. Pat. No. 4,105,031 discloses a simple attachment to provide for an extra collection chamber in a conventional three chambered system. This disclosure does not provide for a two chambered system for use with a regulated suction control or for use without suction.

Summary of the Invention

The present invention overcomes all of the disadvantages noted above with respect to prior art devices and provides a drainage system which may be readily converted from a two chambered system to a three chambered system having suction control. The present invention also provides for minimizing the dead air space normally attendant with use of conventional drainage systems.

According to the present invention there is provided a first container having a collection chamber and an underwater seal chamber which is disposed directly below the inlet to the device. The outlet from the container is connected to the air space above the underwater seal chamber by a passageway having a oneway valve therein. The collection chamber is divided into a plurality of individual compartments with dissolvable seals disposed in each of the compartments so that the dead air space within the container is reduced to a minimum. Liquid flowing from the patient's pleural cavity initially fills the underwater seal and overflows into the collection chamber. The liquid dissolves the seal closing the first compartment and each compartment in the collection chamber is sequentially open as the preceding compartment is filled. The two chambered device can be used without suction with the outlet open to atmosphere or can be used with a regulated suction without the addition of a suction control chamber. There is provided a separable suction control chamber which has a trackway mounted thereon which interfits with a trackway on the first container. The suction control chamber has a needle with a large bore therein which is adapted to pierce a diaphragm on the first chamber so as to add a suction control chamber to the device if required.

There is thus provided an underwater drainage apparatus which may be readily converted from a two chambered system to a three chambered system to meet any operational requirement.

Other objects and many of the attendant advantages of the present invention will become more readily apparent upon consideration of the following detailed description of the preferred embodiment.

BRIEF DESCRIPTION OF THE DRAWINGS

FIG. 1 is an elevational view in section showing the two chambered unit including a collection chamber and underwater seal chamber;

FIG. 1a is a blown up view of the valve shown in FIG. 1;

FIG. 2 is a sectional elevational view of the separate suction control chamber;

FIG. 3 is a diagrammatic view showing the manner of connecting the combined water seal and collection chamber and the suction control chamber and;

FIG. 4 is a diagrammatic view showing the interfitting trackways on the containers.

DETAILED DESCRIPTION OF THE PREFERRED EMBODIMENT

With reference to the drawings, in FIG. 1 there is shown a container 1 which includes a collection chamber and an underwater seal chamber. The structure of this container and the specific details are described and claimed in our copending application filed concurrently herewith. The container is provided with an inlet 2 having a nozzle portion extending outwardly of the container for connection with a thoracotomy tube 3 leading to a patient's pleural cavity. The inlet 2 extends inwardly of the container in the form of a tubular portion 4 which extends to a sump portion 5 of the underwater seal chamber 6. The underwater seal chamber 6 has a sloping bottom wall 7 so that the fluid within the underwater seal drains toward the sump portion 5.

There is provided an outlet 8 which may be open to atmosphere or may be connected with a controlled suction by means of a tube 9. Beneath the outlet is provided a ball valve seat 10 and a ball valve 11 disposed within a cage beneath the seat 10. A chamber 12 is formed beneath the outlet 8 and a passageway 13 extends from this chamber to the air space above the water seal. There is provided a oneway valve 14 disposed in the passageway 13 which permits gasses to be drawn from the underwater seal chamber 6 into the chamber 12 but, which prevents reverse flow. The oneway valve may be a well known Heimlich valve shown in FIG. 1a comprising a pair of resilient elements 14a and 14b normally urged together to a closed position.

The collection chamber is divided into a series of compartments by means of partitions 15, 16 and 17. Each of these partitions has an upper end portion thereof formed with an opening which is normally sealed by a polyvinyl alcohol film 18 for partition 15, seal 19 for partition 16 and seal 20 for partition 17. There is provided a passageway 21 which leads from the underwater seal chamber into the collection chamber and there is a polyvinyl alcohol film seal 22 normally closing this passageway.

In operation the thoracotomy tube is connected with the patient's pleural cavity and fluid flowing from the pleural cavity is collected within the underwater seal chamber and when the underwater seal chamber is filled, it overflows into the passageway 21. The liquid dissolves the seal 22 so that the fluid can flow into the first compartment defined by partition 15. When fluid fills this compartment, the seal 18 is dissolved so that fluid can flow into the next compartment and thus, the compartments of the collection chamber are sequentially filled.

The device shown in FIG. 1 may be used as a two chambered system with the outlet 8 open to atmosphere or with the outlet 8 connected via a tube 9 to a controlled source of suction. Means are provided to readily convert the device shown in FIG. 1 to a three chambered unit including the suction control chamber shown in FIG. 2.

There is provided a rubber diaphragm 23 disposed in the top wall of the container 1 which opens into the chamber 12. This diaphragm is adapted to be punctured by a needle 24 mounted on the bottom wall of the suction control chamber 25 shown in FIG. 2. The needle 24 has a bore therein in communication with a passageway 26 which has the opposite end communicating with the upper end of the large arm 27 of the U-shaped suction control manometer. The small arm 28 of the suction control manometer has the upper end in communication with atmosphere and the lower end of this arm communicates with the bottom of large arm 27 through a sound muffling system 29 which is more fully disclosed in our copending application, Ser. No. 5,512, filed Jan. 22, 1979.

In FIG. 4, it can be seen that interfitting trackways are provided on the container 1 and suction control container 25. The collection chamber and underwater seal chamber 1 has an L-shaped flange 30 thereon which engages a similarly formed groove 31 in the suction control container 25.

When it is desired to provide a suction control chamber on the two chambered apparatus, the containers 1 and 25 are interconnected as shown in FIG. 3. The suction control chamber 25 is then moved downwardly with the trackways 30 and 31 interengaged so that the needle 24 punctures the rubber diaphragm 23 to place the suction control chamber in fluid communication with the chamber 12 disposed beneath the outlet 8. Thus, the two chambered device shown in FIG. 1 may be readily converted to a three chambered system and provide for suction control.

Obviously, many modifications and variations of the present invention are possible in light of the foregoing teachings. What is claimed as new and is desired to be secured by Letters Patent is:

1. An underwater drainage apparatus comprising an integral container having an inlet adapted to be connected to the pleural cavity of a patient, an underwater seal chamber disposed beneath said inlet, a tube extending from said inlet into the lower end of said underwater seal chamber, a collection chamber for receiving fluid overflowing from said underwater seal chamber, an outlet in the upper end of said container, an outlet chamber surrounding said outlet within the container, a passageway interconnecting said outlet chamber with said underwater seal chamber, diaphragm means disposed within said outlet chamber, a separable suction control chamber attachable to said integral container, said suction control chamber including a U tube manometer having a small arm open to atmosphere and a large arm, a passageway extending downwardly from the upper end of the large arm of the U tube manometer and needle means having a bore therethrough disposed at the lower end of said passageway.

2. An underwater drainage apparatus according to claim 1 and further including complementary track means on said integral container and said separable suction control chamber.

3. A package for forming a drainage apparatus with a collection chamber and an underwater seal chamber and a three chambered apparatus including a suction control chamber comprising an integral container having an inlet adapted to be connected to the pleural cavity of a patient, an underwater seal chamber disposed beneath said inlet, a tube extending from said inlet into the lower end of said underwater seal chamber, a collection chamber for receiving fluid overflowing from said underwater seal chamber, an outlet from said container, an outlet chamber surrounding said outlet within the container, a passageway interconnecting said outlet chamber with said underwater seal chamber, diaphragm means disposed within said outlet chamber, a separable suction control chamber including a U tube manometer having a small arm open to atmosphere and a large arm, a passageway extending downwardly from the upper end of the large arm of the U tube manometer and needle means having a bore therethrough disposed at the lower end of said passageway.

4. An underwater drainage apparatus according to claim 3 and further including complementary track means on said integral container and said separable suction control chamber.

5. An underwater drainage apparatus comprising a container including a first container including an inlet opening adapted to be connected to a patient's pleural cavity, a collection chamber in fluid communication with the inlet, an outlet, an underwater seal chamber disposed between the inlet and outlet, a frangible seal in a wall of said container, a trackway on an outer wall of said first container, a separable second container comprising a suction manometer chamber having a needle with a bore therein extending outwardly from a wall of said second container, a trackway on an outer wall of said second container, said trackways on said first and second containers adapted to interfit for sliding engagement between said first and second containers to position said needle on said second container to puncture said seal on said first container to place said first and second containers in fluid communication.

* * * * *